United States Patent
Skorich et al.

(10) Patent No.: US 10,342,467 B2
(45) Date of Patent: Jul. 9, 2019

(54) SEGMENTED SENSOR (71) Applicant: Nonin Medical, Inc., Plymouth, MN (US)

(72) Inventors: Stefan Skorich, St. Louis Park, MN (US); Brian Joseph Kane, Inver Grove Heights, MN (US); Matthew Prior, Plymouth, MN (US)

(73) Assignee: Nonin Medical, Inc., Plymouth, MN (US)

( * ) Notice: Subject to any disclaimer, the term of this patent is extended or adjusted under 35 U.S.C. 154(b) by 0 days.

(21) Appl. No.: 14/644,972

(22) Filed: Mar. 11, 2015

(65) Prior Publication Data
US 2016/0262673 A1 Sep. 15, 2016

(51) Int. Cl.
*A61B 5/1455* (2006.01)
*A61B 5/00* (2006.01)
*A61B 5/024* (2006.01)

(52) U.S. Cl.
CPC ........ *A61B 5/14552* (2013.01); *A61B 5/0002* (2013.01); *A61B 5/02416* (2013.01); *A61B 5/6831* (2013.01); *A61B 5/6832* (2013.01); *A61B 5/0024* (2013.01); *A61B 2562/0223* (2013.01); *A61B 2562/0238* (2013.01); *A61B 2562/04* (2013.01); *A61B 2562/146* (2013.01); *A61B 2562/164* (2013.01)

(58) Field of Classification Search
CPC ... A61B 5/1455; A61B 5/14551; A61B 5/683; A61B 5/6831; A61B 5/6832; A61B 5/6833
See application file for complete search history.

(56) References Cited

U.S. PATENT DOCUMENTS

| 4,942,877 A * | 7/1990 | Sakai | A61B 5/14551 600/323 |
| 5,402,777 A * | 4/1995 | Warring | A61B 5/14552 600/334 |

(Continued)

FOREIGN PATENT DOCUMENTS

WO WO-2010/107913 A2 9/2010
WO WO-2016145155 A1 9/2016

OTHER PUBLICATIONS

"International Application Serial No. PCT/US2016/021714, International Search Report dated Jun. 2, 2016", 4 pgs.

(Continued)

*Primary Examiner* — Eric F Winakur
(74) *Attorney, Agent, or Firm* — Schwegman Lundberg & Woessner, P.A.

(57) ABSTRACT

A device includes a first portion, an information element, a second portion, and an encoder element. The first portion includes a planar substrate and at least one optical element coupled to the substrate. The optical element has an axis and the axis is substantially normal to the substrate. The information element sensor is coupled to the substrate. The information element sensor is configured to provide an information signal. The second portion includes a membrane configured to couple to the planar substrate. The membrane has a contact surface configured to couple with tissue. The encoder element is coupled to the membrane. The information signal corresponds to proximity of the encoder element.

16 Claims, 5 Drawing Sheets

(56) References Cited

U.S. PATENT DOCUMENTS

| | | | |
|---|---|---|---|
| 5,425,375 A * | 6/1995 | Chin | A61B 17/221 |
| | | | 600/549 |
| 6,377,829 B1 | 4/2002 | Al-Ali | |
| 6,515,273 B2 | 2/2003 | Al-Ali | |
| 6,580,086 B1 | 6/2003 | Schulz | |
| 6,920,345 B2 | 7/2005 | Al-Ali | |
| 7,499,739 B2 * | 3/2009 | Sweitzer | A61B 5/14551 |
| | | | 600/323 |
| 7,910,875 B2 | 3/2011 | Al-Ali | |
| 8,233,955 B2 | 7/2012 | Al-Ali et al. | |
| 8,399,822 B2 | 3/2013 | Al-Ali | |
| 8,548,550 B2 | 10/2013 | Al-Ali et al. | |
| 8,706,179 B2 | 4/2014 | Parker | |
| 8,781,549 B2 | 7/2014 | Al-Ali et al. | |
| 8,821,397 B2 | 9/2014 | Al-Ali et al. | |
| 8,860,467 B2 | 10/2014 | Malipatil et al. | |
| 2004/0147822 A1 * | 7/2004 | Al-Ali et al. | 600/323 |
| 2005/0197548 A1 | 9/2005 | Dietiker | |
| 2006/0229510 A1 * | 10/2006 | Fein | A61B 5/14552 |
| | | | 600/323 |
| 2010/0222654 A1 * | 9/2010 | Gonopolskiy et al. | 600/310 |
| 2011/0118694 A1 * | 5/2011 | Yodfat et al. | 604/500 |
| 2013/0030259 A1 | 1/2013 | Thomsen et al. | |
| 2013/0085356 A1 | 4/2013 | Schlottau et al. | |
| 2013/0158372 A1 | 6/2013 | Haisley et al. | |

OTHER PUBLICATIONS

"International Application Serial No. PCT/US2016/021714, Written Opinion dated Jun. 2, 2016", 8 pgs.

\* cited by examiner

SEGMENTED SENSOR

BACKGROUND

Presently available technology for physiological sensors is inadequate. For example, a typical sensor includes high value components that are often discarded after a single use.

OVERVIEW

The present inventors have recognized, among other things, that a problem to be solved can include providing a lower cost sensor system. The present subject matter can help provide a solution to this problem, such as by providing a segmented sensor having a first portion including high value components and a second portion having low value components.

According to one example, the present subject matter includes a sensor module configured to noninvasively measure a physiological parameter. The sensor module can include a first portion and can include a second portion. The first portion can be viewed as a reusable portion that can be used multiple times. This can include multiple usages associated with a single patient or multiple usages with multiple patients. The second portion can be of relatively low cost and, can be construed as disposable.

The second portion of the sensor module includes at least one information element and includes a substantially planar substrate having opposing surfaces. The opposing surfaces include a proximal surface configured to couple with the tissue of the patient and includes a distal surface configured to couple with the first portion of the sensor.

In one example, the first portion of the sensor module includes optical elements such as a radiation emitter and a radiation detector. In addition, the first portion can include an information element sensor. The first portion can include a housing of a protective material such as plastic, silicone, or metal.

The second portion of the sensor module can include an encoder element. The encoder element is configured to communicate wirelessly with the information element sensor in the first portion. The first portion is configured to wirelessly receive information from the second portion, and in this manner, the second portion communicate wirelessly with the first portion of the sensor module. The first portion is electrically isolated from the second portion.

In one example, the encoder element and the information element sensor can communicate using radio frequency communication. For example, the encoder element can include a radio frequency identification (RFID) tag and the information element sensor can include an RFID reader.

In one example, the encoder element and the information element sensor can communicate using magnetic coupling. For example, the encoder can include a magnetic element and the information element sensor can include a Hall Effect sensor.

In one example, the encoder element and the information element sensor can communicate using capacitive coupling. For example, the encoder and information element sensor can each include conductive elements in which case an oscillator circuit is included in the first portion.

In one example, the encoder element and the information element sensor can communicate using inductive sensing, and include a magnet, a metal object, or a conductive element in the second portion, and include a coil in the first portion.

The information element sensor allows the first portion to detect proximity or detect the presence of the second portion. The information element associated with the second portion can be encoded with information pertaining to characteristics of the sensor, such as sensor type. The information element can include encrypted data or security data to prevent reuse or excessive use of the second portion. In addition, the information element can be encoded to indicate authenticity of the second portion.

The first portion and the second portion can have mutually complementary features to allow one to couple with the other through mechanical means. This can include mechanical features in both portions. One example includes an interlocking mechanism by which a deformable feature of one portion engages with a feature of another portion. In one example, an adhesive is disposed on a mating surface of either or both of the first portion and the second portion.

The optical elements of the first portion can include an emitter and a detector. The optical elements of the first portion can be electrically connected with circuitry to allow measurement of a physiological parameter of a patient. This circuitry can be housed in an external (or remote) device such as an oximeter, which connects to the sensor via an electrical connector. The circuitry can be housed in the first portion in which case the measurement data is transmitted wirelessly to an external device such as a computer or a display monitor.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
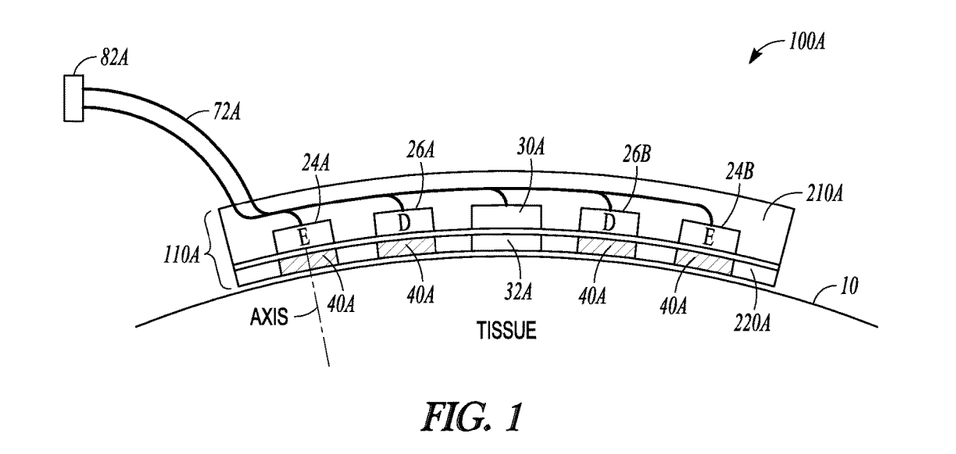
FIG. 1 illustrates a segmented sensor, according to one example.

FIG. 1 illustrates system 100A according to one example. System 100A includes segmented sensor 110A having a first portion 210A and a second portion 220A, according to one example. First portion 210A can be regarded as reusable and second portion 220A can be regarded as disposable however, this view considers only the costs associated with the particular portions.

In the example illustrated, system 100A includes line 72A and connector 82A. Line 72A can include a multiple conductor electric cord or fiber optic link. Connector 82A is configured to engage with a complementary connector of a remote device or an external device. Line 72A and connector 82A can provide electric power for operation of segmented sensor 110A.

In the example illustrated, first portion 210A includes optical elements. The optical elements include emitter 24A and emitter 24B. Emitter 24A and emitter 24B can include an infrared emitter, a near-infrared light emitter, or a visible light emitter. The optical elements of first portion 210A include photodetectors 26A and photodetector 26B. The optical elements are arranged to provide spacing and alignment to enable optical detection of a physiological parameter such as oxygen saturation.

The optical elements, including emitter 24A, emitter 24B, detector 26A, and detector 26B are each connected to line 72A and are each aligned such that an axis is substantially normal to a planar substrate of first portion 210A. In the example, the optical elements of first portion 210A can be viewed as coupled to a planar substrate disposed along a bottom surface.

First portion 210A includes information element sensor 30A, which is connected to line 72A. Information element sensor 30A is configured to read data or detect proximity associated with information encoder 32A of second portion 220A.

Second portion 220A includes a membrane. In one example, the membrane is coupled to tissue 10 by an adhesive. In the example shown, tissue 10 has a curvature to represent, for example, a scalp. In other figures, the curvature is omitted for clarity and the second portion is shown having a flat contour. The second portion can be rigid or flexible and conformable to accommodate a tissue contour.

Second portion 220A is also coupled to first portion 210A via an adhesive or via a mechanical feature.

Second portion 220A includes a plurality of openings or windows, each of which are here denoted as aperture 40A. Aperture 40 can include an optically transparent window or a cutout portion of a membrane.

Figure 2A:
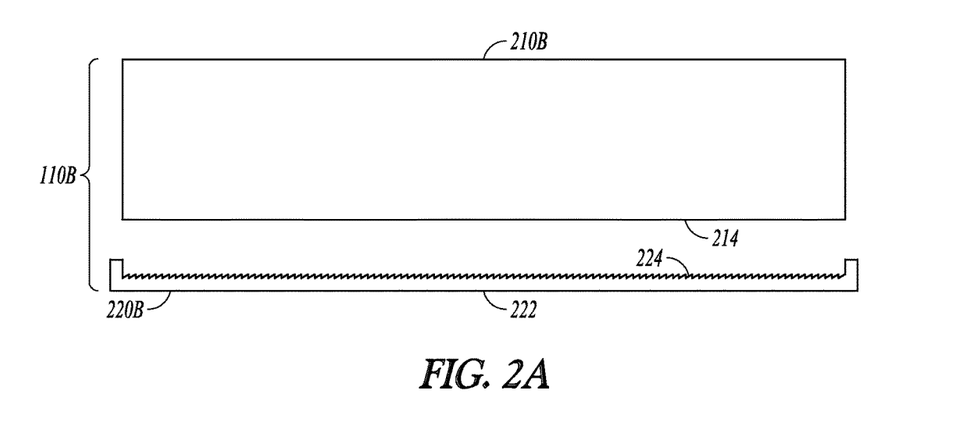
FIG. 2A illustrates an interface for a segmented sensor, according to one example.

FIG. 2A illustrates an interface for segmented sensor 110B, according to one example. First portion 210B includes mating surface 214. Second portion 220B includes tissue surface 222 and mating surface 224. Mating surface 214 and mating surface 224 can be bonded by an adhesive (here denoted by a jagged surface) affixed to either one or both.

In one example, tissue surface 222 is coupled to patient tissue by an adhesive bond. In other examples, tissue surface 222 of second portion 220B is coupled, or held securely, to the patient by a strap, a belt, a headband, an elastic wrap, a bandage wrap, or a sleeve.

Figure 2B:
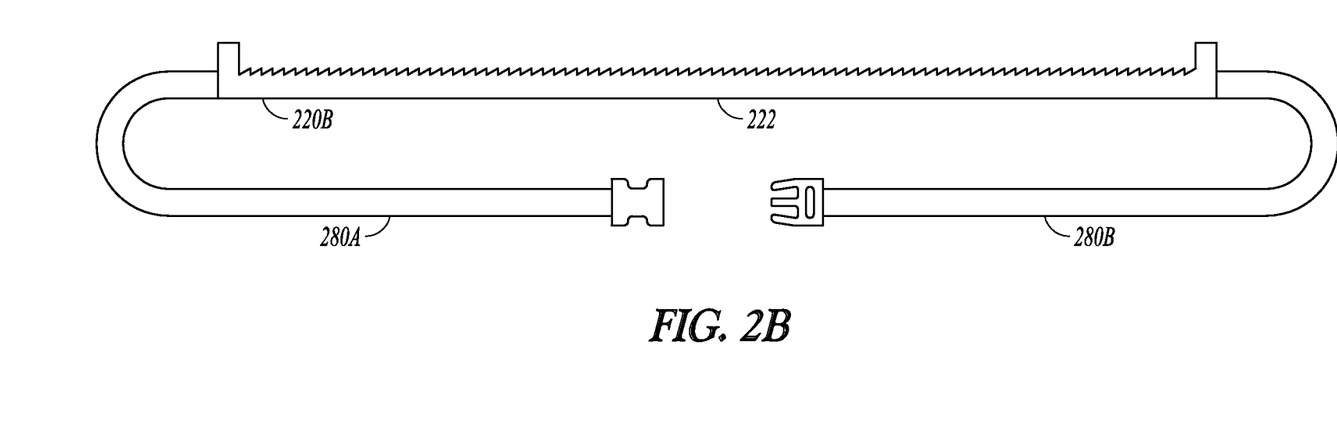
FIG. 2B illustrates a second portion having a mechanical fastener, according to one example.

FIG. 2B illustrates second portion 220B having a mechanical fastener. In the figure, mechanical fastener is represented by a strap having portion 280A and portion 280B, configured to encircle a patient body. Portions 280A and 280B terminate in buckle ends or other fastener. In addition to a strap, the mechanical fastener can include a belt, a headband, an elastic wrap, a bandage wrap, or a sleeve. The mechanical fastener is configured to couple the second portion to the tissue of the patient. The coupling between the patient and the second surface is configured to occlude ambient light and provide good optical coupling to the tissue.

Figure 3A:
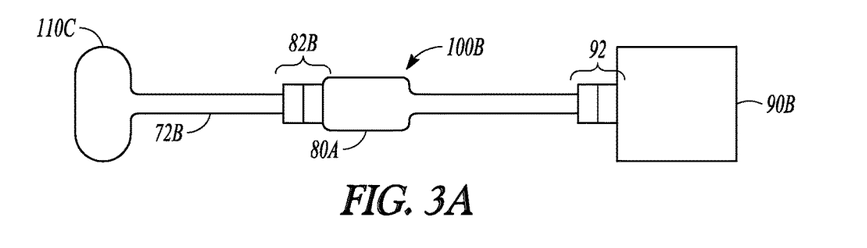
FIG. 3A illustrates a wired system including an interconnected segmented sensor, according to one example.
Figure 3B:
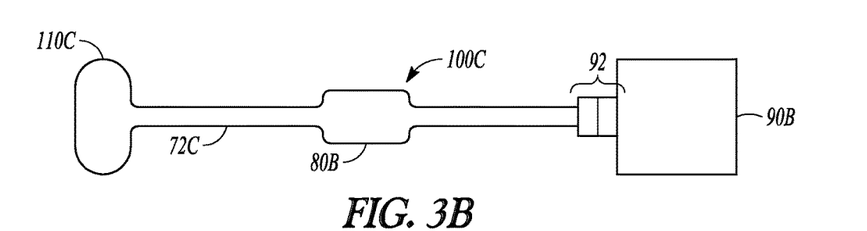
FIG. 3B illustrates a wired system including a segmented sensor, according to one example.
Figures 3C, 4:
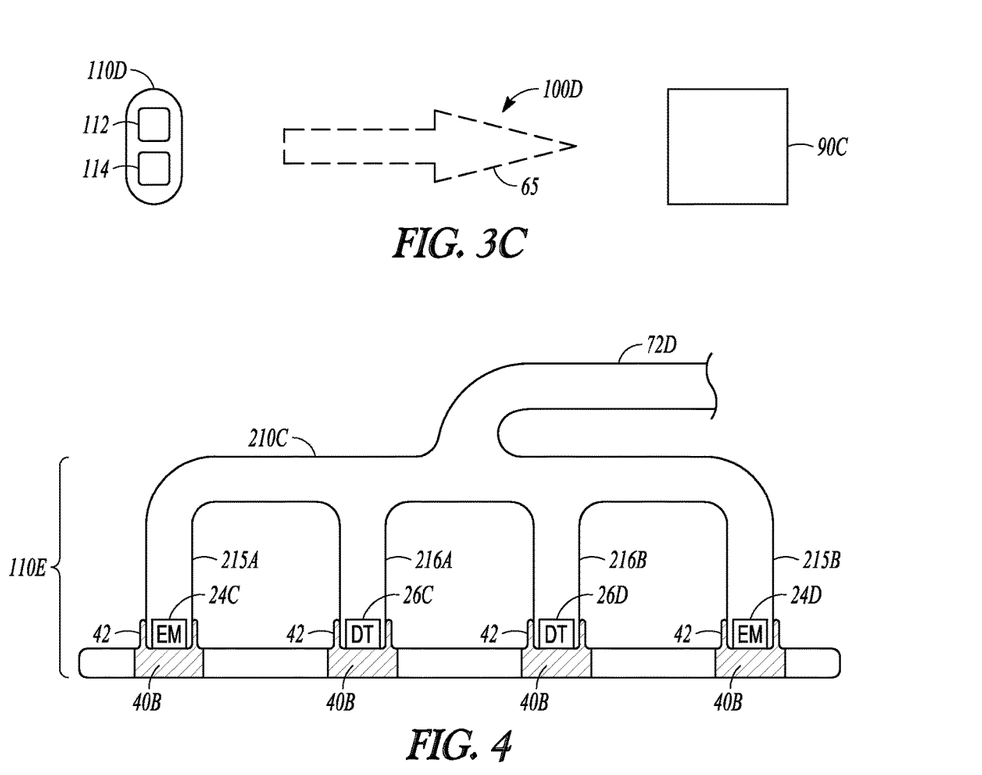
FIG. 3C illustrates a wireless system including a segmented sensor, according to one example.
FIG. 4 illustrates a segmented sensor, according to one example.

FIGS. 3A, 3B, and 3C illustrate configurations of systems according to various examples.

FIG. 3A illustrates system 100B having wired interconnections. In the figure, segmented sensor 110C is coupled to device 80A by link 72B and by connector 82B. Device 80A can include an oximeter having measurement circuitry. Device 80A can control operation and receive data from segmented sensor 110C. Device 80A is coupled to device 90B by connector 92. Device 90B can include a display or a computer.

FIG. 3B illustrates system 100C including a sensor with an integrated oximeter. System 100C includes wired interconnections as shown. In the figure, segmented sensor 110C is coupled to device 80B by link 72C. Device 80B can include measurement circuitry. Device 80B can control operation and receive data from segmented sensor 110C. Device 80B is coupled to device 90B by connector 92. Device 90B can include a display or a computer.

FIG. 3C illustrates system 100D having wireless interconnections. In the figure, segmented sensor 110D is coupled to device 90C by wireless link 65. Device 90C can include a display. Device 90C can control operation and receive data from segmented sensor 110D. Segmented sensor 110D includes wireless communication module 112 and measurement module 114. In one example, segmented sensor 110D includes an oximeter and measurement module 114 includes measurement circuitry. Segmented sensor 110D communicates with device 90C the processed data by a radio frequency communication link or other non-wired communication link.

FIG. 4 illustrates segmented sensor 110E, according to one example. Segmented sensor 110E includes first portion 210C and second portion 220C. First portion 110E includes an arrangement of optical elements disposed on flexible members. For example, emitter 24C is disposed at an end of linear member 215A, emitter 24D is disposed at an end of linear member 215B, detector 26C is disposed at an end of linear member 216A and detector 26D is disposed at an end of linear member 216B. Emitter 24C is coupled to second portion 220C at aperture 40B by socket 42. In addition, detector 26C is coupled to second portion 220C at aperture 40B by socket 42.

Linear members 215A, 215B, 216A, and 216C are flexible and can be manipulated to engage with sockets of second portion 220C in the manner shown. The sockets of second portion 220C are aligned with apertures and are configured to receive the limbs and establish suitable spacing. The spacing can be selected according to the patient age, site, health, or other parameter.

Figure 5:
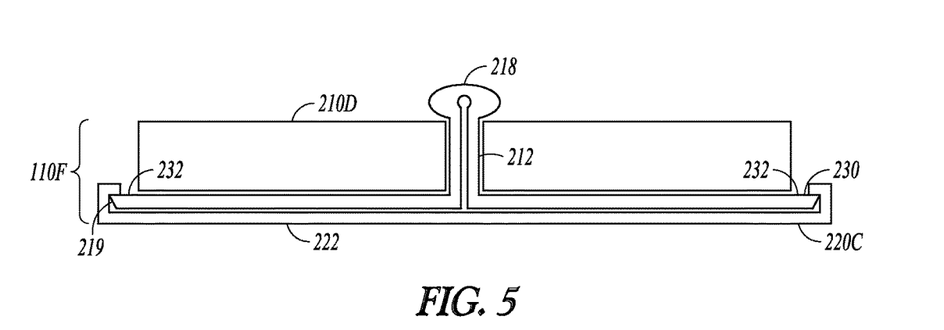
FIG. 5 illustrates a segmented sensor having a user separable linkage, according to one example.

FIG. 5 illustrates segmented sensor 110F having a user-separable linkage, according to one example. First portion 210D includes an aperture to receive stem 212. Stem 212, affixed to coupler plate 230, includes a split member that terminates with bulb 218 on one end and is coupled to second portion 220C at the other end. Second portion 220C includes tissue surface 222 and beveled feature 219. Second portion 220C and first portion 210D are coupled together by forcing bulb 218 through an aperture of first portion 210D. Beveled feature 219, located at each end 232 of coupler plate 230, is configured to receive an adhesively bonded membrane.

First portion 210D and second portion 220C are configured to allow single-time usage. After assembly in the manner shown in the figure, segmented sensor 110F is configured to resist separation without damage. As such, bulb 218 will separate from stem 212 if physically forced apart. In this manner, repeated usage of second portion 220C is precluded.

Figure 6:
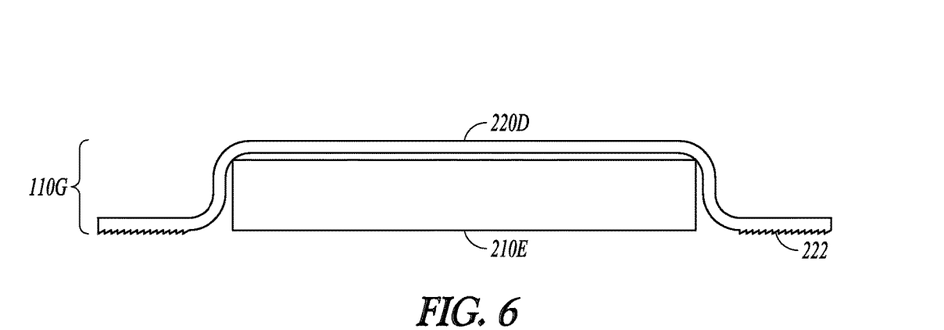
FIG. 6 illustrates a segmented sensor having an overlay, according to one example.

FIG. 6 illustrates segmented sensor 110G having second portion 220D configured as an overlay, according to one example. In this example, first portion 210E includes optical elements and an information element sensor. Second portion 220D includes adhesively bonded tissue surfaces 222 and information encoder. Second portion 220D engulfs first portion 210E.

Figure 7:
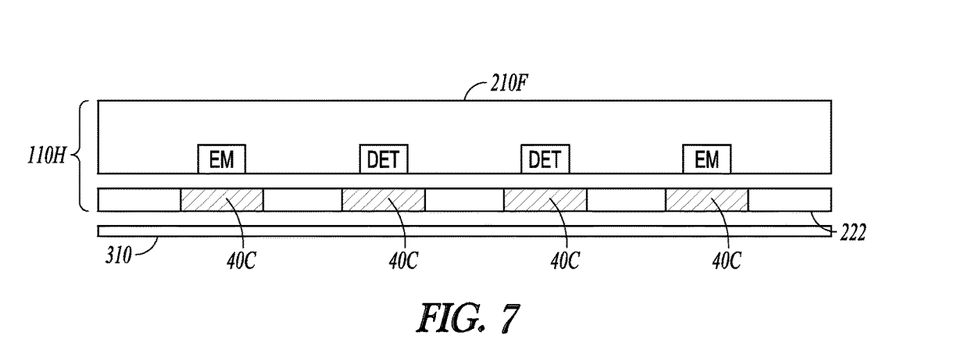
FIG. 7 illustrates a segmented sensor having a protective layer, according to one example.

FIG. 7 illustrates segmented sensor 110H having protective layer 310, according to one example. First portion 210F includes emitters and detectors as shown. Second portion 220E includes apertures 40C aligned with the optical elements of first portion 210F. In addition, protective layer 310 is adhesively bonded to the tissue surface 222 of second portion 220E. The configuration shown is suitable for storage or shipping.

Figure 8:
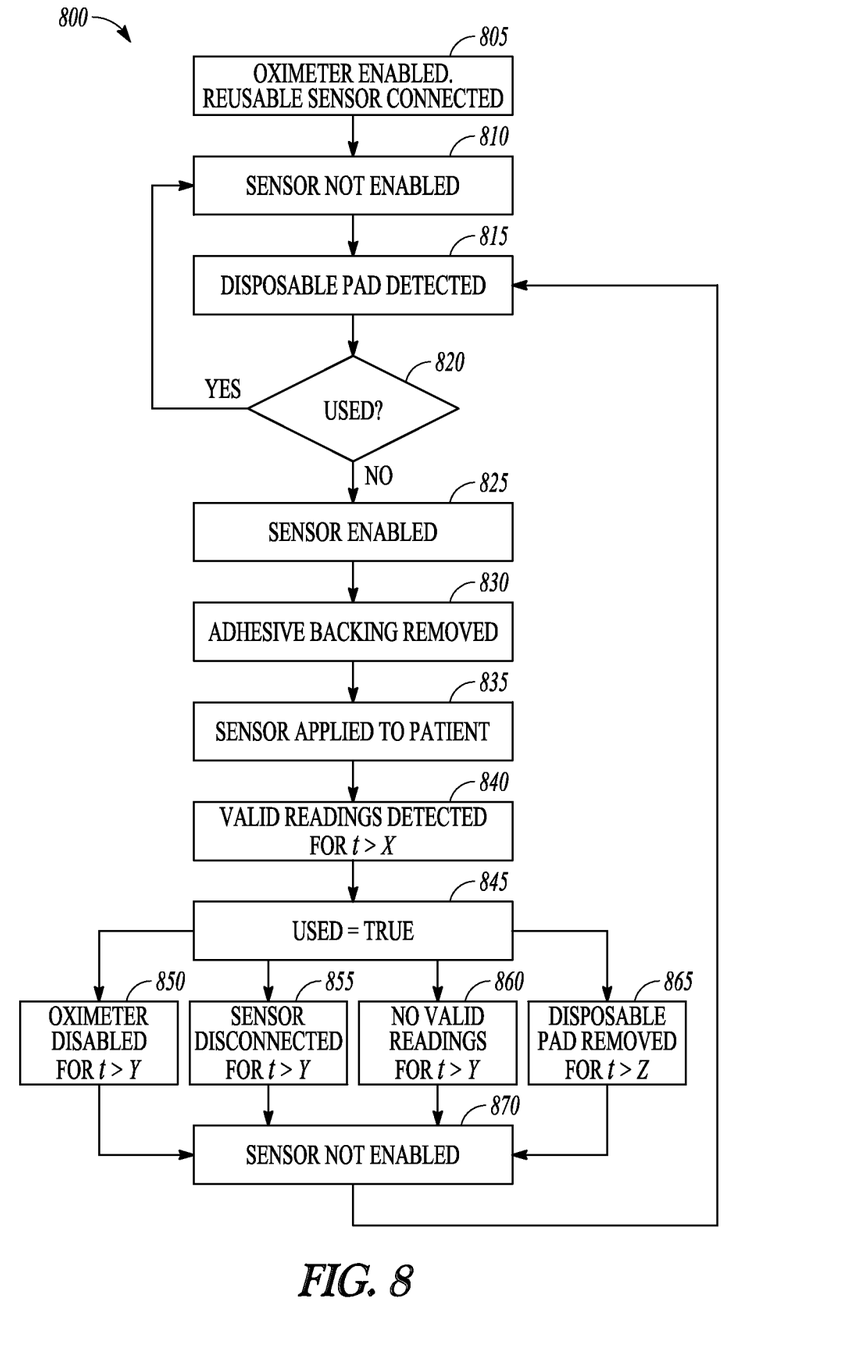
FIG. 8 shows a validation scheme for a segmented sensor, according to one example.

FIG. 8 illustrates method 800 according to one example. Method 800 includes a validation scheme for a segmented sensor. Method 800, at 805 includes enabling a remote device (such as an oximeter) and includes coupling the segmented sensor with the remote device.

At 810, the method indicates the state in which the segmented sensor is not enabled.

At 815, the method includes monitoring for the information element. This can include detecting presence or proximity.

At 820, method 800 includes an inquiry to determine if the segmented sensor has been used previously. This can include checking a counter value, checking a date or time code, or checking status of a fusible element. If the inquiry indicates that the segmented sensor has been used previously, then processing continues at 810 where the flag or state is set to indicate that the sensor is not enabled. If the inquiry returns a negative answer, then, at 825, processing continues by setting a flag to indicate that the sensor is enabled.

At 830, method 800 includes removing a backing film from an adhesive layer on the second portion of the segmented sensor.

At 835, method 800 includes applying the segmented sensor to the patient tissue.

At 840, method 800 includes an inquiry to determine if the segmented sensor has returned a valid reading for a time greater than value X.

If the inquiry at 840 indicates that the sensor has been used, then, at 845, method 800 includes setting a flag to indicate that the sensor has been used previously. Further inquiries are presented at 850, 855, 860, and at 865. At 850, the inquiry considers if the oximeter has been disabled for time greater than a selected value Y. At 855, method 800 can include an inquiry to consider if the sensor has been disconnected for a time greater than a selected value Y. At 860, method 800 can include an inquiry to determine if the segmented sensor has provided invalid readings for a time greater than a selected value Y. At 865, method 800 includes an inquiry to consider if the second portion has been removed for a time greater than selected value Z.

If any inquiry presented at 850, 855, 860, or 865 provides a 'true' indication, then, at 870, the segmented sensor is disabled and thereafter, processing returns to 815.

Other validation routines are also contemplated, including different inquiries and different processing.

An example of the present subject matter utilizes a wireless communication link between a first portion and a second portion. The wireless communication link can include a rolling security protocol in which each information or data exchange includes a different encoding. In one example, a segmented sensor system includes a counter that is incremented to monitor usage instances or includes a timer to monitor usage duration. On detecting a predetermined count or time, the segmented sensor is disabled.

The optical elements of a segmented sensor can be configured to measure and monitor regional oximetry, pulse oximetry, DC-based parameter (such as a signal amplitude), or other measured physiological parameter.

In various examples, the second portion can include zero, one, two or more optical elements. In various examples, the first portion can include zero, one, two or more optical elements.

The second portion can include a substrate having opposing surfaces in which one surface can be affixed to tissue and another surface can be coupled to the first portion.

The first portion can include a housing to which is coupled the optical elements. The optical elements are affixed to a bottom surface and are aligned to interact with the tissue. The housing can include a protective material such as plastic or silicone.

In one example, the first portion and the second portion are wirelessly coupled to enable functionality. Failure to wirelessly couple in the manner provided will preclude operability of the segmented sensor.

The segmented sensor can be connected to circuitry that enables the measurement of physiological parameters of the patient. This circuitry can be contained in an external device such as an oximeter, which connects to the sensor via an electrical connector in the reusable portion. The circuitry can be contained in the first portion of the sensor itself, with the measurement data being transmitted wirelessly to an external device such as a computer or a display monitor.

The first portion and the second portion of the segmented sensor can be removably attached to each other. The second portion of the sensor carries the sensor to the patient using an adhesive layer.

In one example, the segmented sensor includes a tissue contact surface on a bottom of the second portion and a mating surface configured to engage with a bottom surface of the first portion. The second portion includes windows aligned with the emitters and detectors of the first portion that allows the radiation to pass through unimpeded.

The first portion and the second portion are held in alignment by an alignment feature. The alignment feature can provide visual indication (such as a visible light), audible indication (an audible tone), a tactile (a snap fit), or a combination. One example includes an alignment feature at the mating surface between the first portion and the second portion. The alignment feature can include a pin, a tab, a hole, a ridge, or other element that ensures alignment of the optical element of the first portion and the aperture of the second portion. An alignment feature can include a raised perimeter, an example of which is shown in FIG. 2A and in FIG. 2B. In addition to aligning the optical element and the aperture, the alignment feature can also mechanically secure the first portion to the second portion. For example, FIG. 5 illustrates bulb 218 and beveled features 219 which engage corresponding features to provide alignment and also secures the first portion to the second portion.

In one example, the mating surface of the second portion includes an adhesive layer that adheres to the bottom surface of the first portion. To attach the second portion to the first portion, an adhesive liner is removed from the second portion, thus exposing the adhesive. The second portion is aligned and coupled to the first portion. After using the segmented sensor, the second portion can be peeled off the first portion.

To aid in this removal, a tissue contact surface of the second portion contains an adhesive layer that bonds to the patient. The adhesive bond on the tissue is stronger than the mating surface bond between the first portion and the second portion, so that when the segmented sensor is removed from the patient, the second portion separates from the first portion and remains affixed to the patient.

In one example, the first portion or the second portion includes a tab and the user can grasp and pull the tab to separate the portions.

In one example, a region of the adhesive contains a non-stick surface (for example, PTFE), such that no adhesive residue remains when the second portion is removed.

In one example, the second portion and the first portion include mating features that provides a locking interface. To attach the second portion to the first portion, the locking features of the two portions are mated and a lock is engaged. According to various examples, this can include a retractable protrusion in the first portion that mates with a cavity in the second portion. Upon insertion of the first portion into the second portion, the protrusions are forced into a refracted position, similar to the action of a door latch, and once fully inserted, the protrusions snap into place with an audible click. A mechanism on the first portion, such as a button, knob, or lever, retracts the protrusions to allow for removal of the second portion.

In one example, a retractable protrusion in the first portion mates with a cavity in the second portion. A knob on the first portion adjusts the protrusions between a protruded position and a retracted position. Upon insertion of the first portion into the second portion, the knob holds the protrusions in the retracted position. After insertion, the knob is adjusted to the protruded position, locking the first portion in place. In one example, after the second portion is locked in place, retracting the protrusions results in the destruction of the cavities, such that a used second portion cannot be locked to the first portion again.

In one example, the second portion includes a laminated stack of adhesive layers, with the bottom-most layer contacting the patient tissue and sticking to the patient during use. After each use, the bottom-most adhesive layer is removed and thus exposing a fresh adhesive layer.

In one example, the second portion and the first portion includes mating features that create a friction-fit interface. To attach the second portion to the first portion, the two portions are pressed together, forcing the friction-fit mating features together. In one example, this includes a tongue-in-groove configuration. In one example, this includes a raised outer radius on the second portion that captures the perimeter of the first portion. In one example, a raised cylindrical node is configured to fit into a matching recess, similar to children's plastic bricks. In one example, the second portion and the first portion include mating features that snap together. To attach the second portion to the first portion, the two portions are pressed together, snapping the mating features together. For example, the interface can include a spline configured to engage a groove, a snap-fit element, or the second portion includes snap-fit hooking posts protruding from the mating surface, and the first portion includes recessed areas around the perimeter, such that when the first portion is pressed into the second portion, the perimeter of the first portion is captured in place by the hooking posts.

In one example, the second portion and the first portion mate together using a magnetic interface. One portion includes a magnet, such as high-pull rare earth magnet, and the other portion includes a piece of ferromagnetic material, such as iron.

In one example, the second portion has a larger footprint than the first portion and the second portion is applied over the top of the first portion, such that the first side of the second portion contacts both the patient tissue and a top side of the first portion. The surface of the second portion extends beyond the perimeter of the first portion and contains an adhesive layer that bonds to the patient and holds the segmented sensor in place. The second portion and the first portion can be attached together using a variety of couplings.

In one example, the second portion forms an envelope or sleeve which surrounds the first portion. The sleeve is sealed closed around the first portion. This sealing could be accomplished through a variety of features, including a hook-and-loop strip, adhesive, or a locking strip similar to those used in a zip top plastic bag. The second portion contains windows aligned with the emitters and detectors of the first portion that allow the radiation to pass through unimpeded. The first portion and the second portions can be coupled using a variety of coupling features.

The spacing and arrangement of optical elements (for example, the distance between the emitters and detectors) remains static and is set by the construction of the first portion. A variety of different sensor spacing can be provided, such as 20 mm spacing for an adult patient, and 15 mm spacing for a pediatric patient. In one example, the segmented sensor includes user-selectable spacing and arrangement of optical elements. In one example, the emitters and detectors are disposed at the end of flexible "fingers" which couple with receptacles in the second portion.

In one example, the second portion includes "pipes" which guide the radiation from the emitters and detectors, configured for a particular spacing, to emission and detection sites on the patient in a different spacing. The pipes can be fabricated of optical fibers or clear plastic.

The attachment configuration between the first and second portion can allow multiple shapes of the second portion, such that site-specific shapes are available to the end user. For example, a segmented sensor for the forehead may include a different adhesive shape than a segmented sensor for a calf muscle.

In one example, the second portion includes at least one information element, and the first portion includes at least one sensing element. The sensing element in the first portion detects and/or communicates with the information element in the second portion without requiring electrical contact between the two elements. In one example, the coupling includes radio frequency signaling. An RFID tag in the second portion communicates with an RFID reader in the first portion. In one example, a magnetic sensor is provided. A magnetic element in the second portion and a Hall Effect sensor in the first portion can provide a wireless coupling. One example includes a capacitive sensing configuration, such as conductive elements in the first and second portions, coupled with an oscillator circuit. One example includes an inductive sensing configuration, such as a conductive element in the first portion, and a coil in the second portion. One example includes an optical signaling configuration, such as an LED coupled with a microcontroller and an energy source in the second portion, and a photodiode in the first portion.

The information element allows the first portion of the segmented sensor to detect the presence of the second portion. The information element can include information pertaining to characteristics of the segmented sensor, such as sensor type. The information element can include security measures such as encryption to unsure quality of second portions.

Various Notes & Examples

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A device comprising:
   a first portion having a planar substrate and having at least one optical element coupled to the substrate, the optical element configured to emit or detect light aligned substantially normal to the substrate, the first portion having an electrical circuit;
   an information element sensor coupled to the substrate;
   a second portion having a membrane configured to couple to the planar substrate, the membrane having a contact surface configured to couple with tissue wherein the membrane is configured to occlude ambient light and wherein the membrane includes at least one transparent aperture aligned with the at least one optical element and wherein the aperture is configured to pass optical radiation between the at least one optical element and the contact surface;
   an encoder element coupled to the membrane; and
   wherein the circuit is configured to read data from the encoder element or configured to detect proximity of the encoder element relative to the information element sensor and wherein the circuit is configured to enable or disable the at least one optical element based on a wireless coupling between the first portion and the second portion and based on information encoded in the encoder element.

2. The device of claim 1 wherein the contact surface includes an adhesive.

3. The device of claim 1 wherein the optical element is configured to emit radiation.

4. The device of claim 1 wherein the optical element is configured to detect radiation.

5. The device of claim 1 wherein the optical element includes at least one radiation emitter and at least one photodetector and wherein the photodetector is configured to provide an electrical signal corresponding to oximetry.

6. The device of claim 1 wherein the encoder element includes at least one of a magnet, a capacitor plate, a metal object, and a radio frequency identification device.

7. The device of claim 1 wherein the information element sensor includes at least one of a magnet sensor, a capacitor plate, an inductor, and a radio frequency identification device reader.

8. The device of claim 1 wherein the membrane includes a mechanical alignment feature configured to engage with the planar substrate.

9. The device of claim 1 further including a wireless communication module coupled to the first portion, wherein the wireless communication module is configured to communicate wirelessly with a remote device.

10. A method comprising:
coupling an electrical circuit and an optical element to a first portion having a planar substrate, the optical element configured to emit or detect light aligned substantially normal to the substrate;
coupling an information element sensor to the substrate;
configuring a second portion having a membrane to couple with the planar substrate, the membrane having an adhesive surface configured to bond with tissue and wherein the membrane is configured to occlude ambient light and wherein the membrane includes a transparent aperture aligned with the optical element and wherein the aperture is configured to pass light between the optical element and the adhesive surface;
coupling an encoder element to the membrane; and
wherein the circuit is configured to read data from the encoder element or configured to detect proximity of the encoder element relative to the information element sensor and wherein the circuit is configured to enable or disable the optical element based on a wireless coupling between the first portion and the second portion and based on information encoded in the encoder element.

11. The method of claim 10 further including configuring the optical element to emit radiation.

12. The method of claim 10 further including configuring the optical element configured to detect radiation.

13. The method of claim 10 further including configuring the optical element to provide a signal corresponding to at least one of regional oximetry, pulse oximetry, or a DC-based parameter.

14. The method of claim 10 wherein coupling the encoder element includes coupling at least one of a magnet, a capacitor plate, an inductor, and a radio frequency identification device.

15. The method of claim 10 wherein coupling the information element sensor to the substrate includes coupling at least one of a magnet sensor, a capacitance sensor, an inductance sensor, and a radio frequency identification device reader.

16. The method of claim 10 further including coupling a wireless communication module coupled to the first portion, wherein the wireless communication module is configured to communicate wirelessly with a remote device.

* * * * *